United States Patent [19]

Wygant et al.

[11] 4,390,842
[45] Jun. 28, 1983

[54] FLUID CONDUCTIVITY DEVICE FOR MEASURING FLUID VOLUMES AND METHOD THEREFOR

[75] Inventors: N. Duane Wygant, Sedalia; Stanley C. Jones, Littleton, both of Colo.

[73] Assignee: Marathon Oil Company, Findlay, Ohio

[21] Appl. No.: 219,562

[22] Filed: Dec. 23, 1980

[51] Int. Cl.³ .............................................. G01N 27/02
[52] U.S. Cl. .................................. 324/439; 324/71.4
[58] Field of Search .................. 324/71 CP, 425, 439; 235/92 PC

[56] References Cited

U.S. PATENT DOCUMENTS

| | | | |
|---|---|---|---|
| 2,599,413 | 6/1952 | Reichertz | 175/183 |
| 3,701,006 | 10/1972 | Volkel et al. | 324/30 |
| 4,063,309 | 12/1977 | Hennessy | 324/71 CP |

Primary Examiner—Michael J. Tokar
Attorney, Agent, or Firm—Jack L. Hummel

[57] ABSTRACT

The invention provides a device and method for measuring the volumes of oil (310) and water (320) in an oil and water mixture (300) wherein the mixture (300) flows at a constant volumetric flow rate. The device includes a formed cylindrical passageway (200) capable of receiving the fluid mixture (300) and for separating the fluid mixture (300) into separate oil and water droplets (310, 320) while maintaining the constant volumetric flow rate. Electrical probes (400) mounted across the passageway (200) are interconnected with an alternating current source (1200) to apply current to the flowing oil and water droplets in the passageway (200). The resulting sinusoidal voltage pulses (1300, 1310) produced by the flowing oil and water droplets are compared to a predetermined voltage level (1320) and if a water droplet (320) passes the probes (400), the sinusoidal voltage pulses (1310) exceed the predetermined level (1320) and these pulses are then counted (1240). If the sinusoidal electrical pulses (1300) are less than the predetermined level (1320) due to the low conductivity of the oil droplet (310), then no output pulses are generated and the counter (1240) remains inactive. The pulse information provided provides a time difference between the leading (500) and lagging (510) interfaces of each droplet between the oil droplets and the water droplets and the measured time difference is proportional to the volume of the droplets.

12 Claims, 13 Drawing Figures

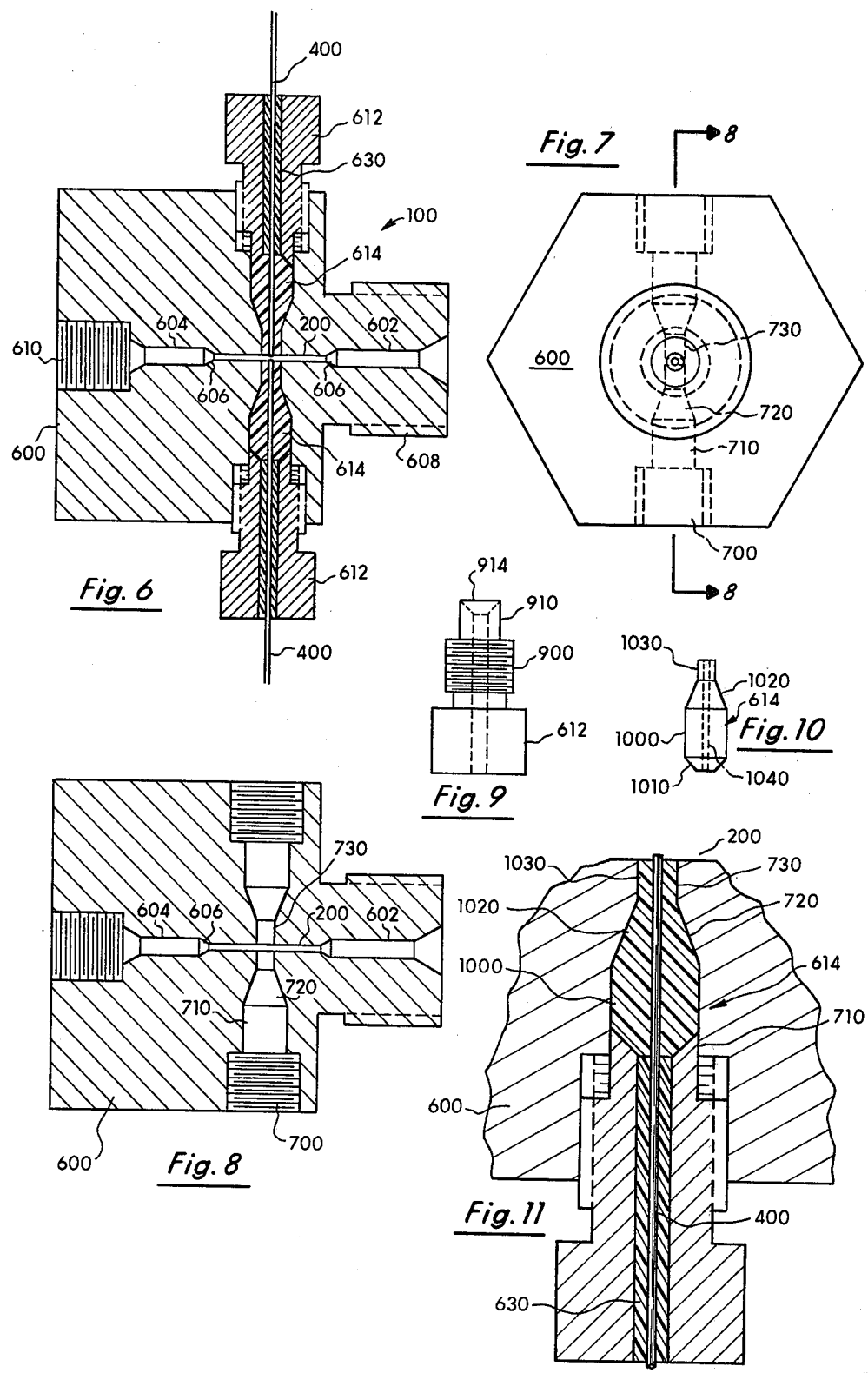

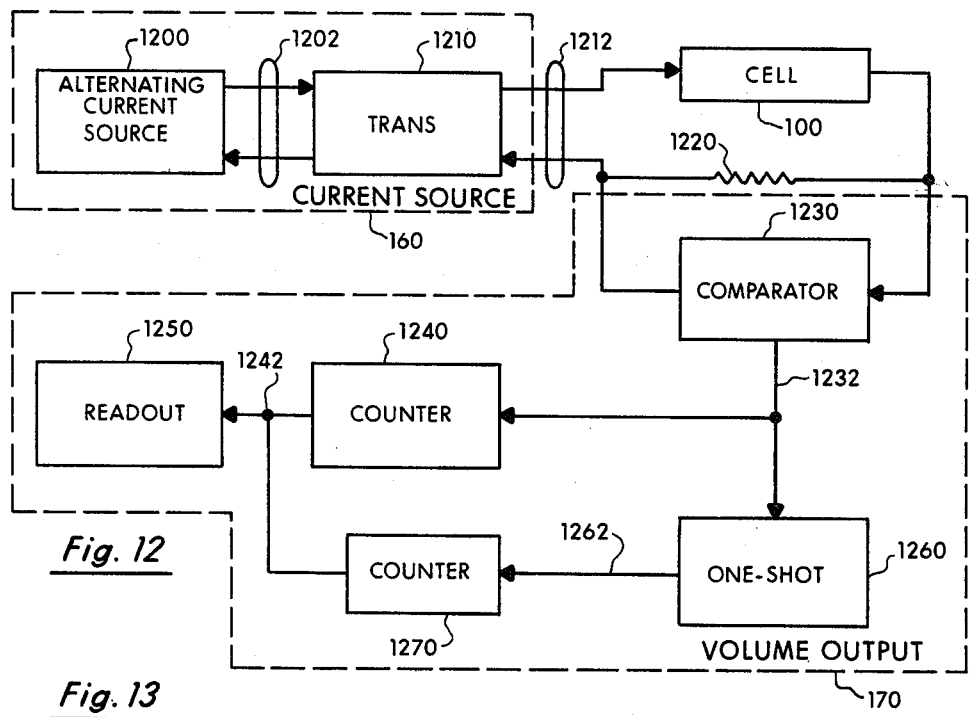
*Fig. 12*
*Fig. 13*
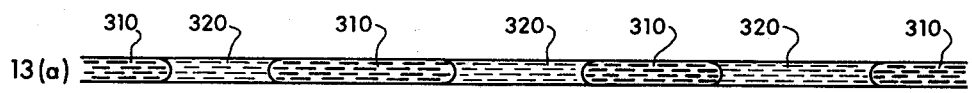
13(a)
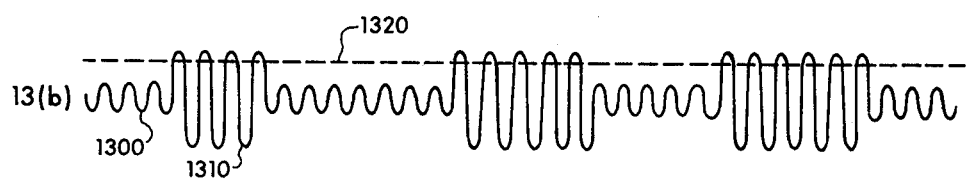
13(b)
13(c)
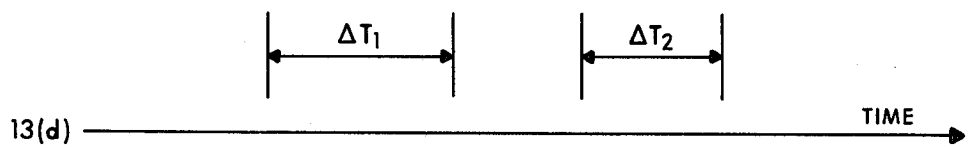
13(d)
13(e)

FLUID CONDUCTIVITY DEVICE FOR MEASURING FLUID VOLUMES AND METHOD THEREFOR

TECHNICAL FIELD

The present invention relates to methods and devices for measuring the volumes of individual fluids in a fluid mixture and, more particularly, to methods and devices for measuring the volumes of oil and water in an oil/water mixture produced in relative permeability measurements of sub-strata cores.

BACKGROUND ART

In relative permeability measurements involving crude oil and brine, it becomes necessary to measure the volume of crude oil produced from sub-strata cores in relation to the total fluids produced. In low pressure/low temperature measurements the effluent fluid mixture from the core is collected in glassware at atmospheric pressure and the relative volumes can be calculated. The use of glassware, however, for high pressure/high temperature measurements involving volatile crude oil, is not practical since such fluids when collected would volatilize and would also change in density. No prior art technique or device is known for measuring volumes at high pressures and temperatures which result in measurements free from fluid expansion and vaporization errors.

A patentability search was conducted and the following patents were uncovered:

| U.S. Pat. No. | Inventor | Issue Date |
| --- | --- | --- |
| 3,701,006 | George D. Volkel, et al | 10-24-72 |
| 2,599,413 | P. P. Reichertz | 6-3-52 |

The 1952 patent issued to Reichertz (U.S. Pat. No. 2,599,413) relates to a resistivity meter for analyzing drilling and composition. Reichertz utilizes a frequency of operation in the low audio range of approximately 100 cycles per second using 90 volt batteries. The Reichertz resistivity cell contemplates a mixture of a number of different fluids including brine, oil, and drilling mud to generate an overall average value of resistivity of a particular, in time, composition of the fluids in the cell.

The 1972 patent issued to Volkel, et al. (U.S. Pat. No. 3,701,006) also relates to an apparatus for measuring the electrical resistivity of flowing drilling mud. The Volkel approach offers an improvement over the Reichertz approach in that the resistivity measuring system easily retrofits into conventional drilling mud supply systems. Volkel utilizes an elongated non-conductive tubular conduit through which a flowing stream of drilling mud is directed. An electrical current is operatively provided to pass through the flowing mud. Volkel utilizes alternating current source operating in the range of about 60 to 2000 cycles per second. Again, the Volkel approach is used to measure a composite of oil, brine, drilling mud, and other particular materials mixed together.

Neither of the above patented approaches are suitable for the precise volume determinations for oil-water permeability measurement.

DISCLOSURE OF INVENTION

The problem faced in high pressure/high temperature relative permeability measurements involving volatile crude oil and brine or water is to measure accurately the cumulative volume of crude oil produced from a sub-strata core as a function of the total fluid produced through the core without having any of the fluid volatilize or undergoing any changes in density.

The fluid conductivity device of the present invention provides a solution to the problem and includes a cylindrically formed passageway through which the fluid mixture containing oil and water under high temperature and high pressure is received and is separated into discrete oil and water droplets, two opposing electrical probes connected across the interior of the passageway for applying current from an alternating current source to the oil and water droplets passing through the passageway wherein the electrical probes are oriented in a plane substantially perpendicular to the flow of the droplets, a comparator circuit receptive of the voltage signals across a current sensing resistor in series with the probe for producing a first signal representative of water when the voltage signals exceed a predetermined threshold level and for producing a second signal representative of oil when electrical signals are below the predetermined threshold level, and an electrical counter for counting the number of first signals wherein the total count is proportional to the time difference between the leading and lagging interfaces of each droplet as the droplet flows past the probe. The measured time difference being proportional to the volume of each droplet.

The method of measuring the volume of oil and water in an oil and water mixture includes the steps of separating the mixture into separate oil and water droplets while maintaining a constant volumetric flow rate, sensing the leading and lagging interfaces of each separated droplet in order to determine the volume of the droplet by detecting electrical conductivity of the droplet, and measuring the time difference between the leading and lagging interfaces so that the volume of the droplet can be determined.

In comparison to the conventional prior art approaches based upon the results of the patentability search, the present invention separates the oil and water flowing mixture into separate oil and water droplets in a small diameter tube or passageway so that the electrical conductivity (or resistivity) can be utilized to accurately measure the volume of each droplet as it flows through the passageway. The prior art approaches, to the contrary, do not provide such separation and do not teach measuring the time difference between the leading and lagging interfaces of each unique droplet. Rather, the prior art approaches provide an accumulative reading based upon the average or overall resistivity of the mixture, not the separate fluids contained therein.

BRIEF DESCRIPTION OF THE DRAWING

The details of the present invention described in the accompanying drawing:

FIG. 6 is a cross-sectional view of the conductivity cell of the present invention;

FIG. 7 is a top view of the cell body of the present invention;

FIG. 8 is a cross-sectional view through the cell body of FIG. 7;

FIG. 9 is a side view of the compression nut of the present invention;

FIG. 10 is a side view of the ferrule of the present invention;

FIG. 11 is an enlarged partial cross-sectional view showing the compression nut engaging the ferrule to orient and hold an electrical probe of the present invention;

FIG. 12 is an electrical block diagram illustrating the interconnection of the electronic circuits; and FIG. 13 is a set of graphic representations illustrating the relationship of the conductivity cell of the present invention with the electronics of FIG. 12.

BEST MODE FOR CARRYING OUT THE INVENTION

Figure 1:
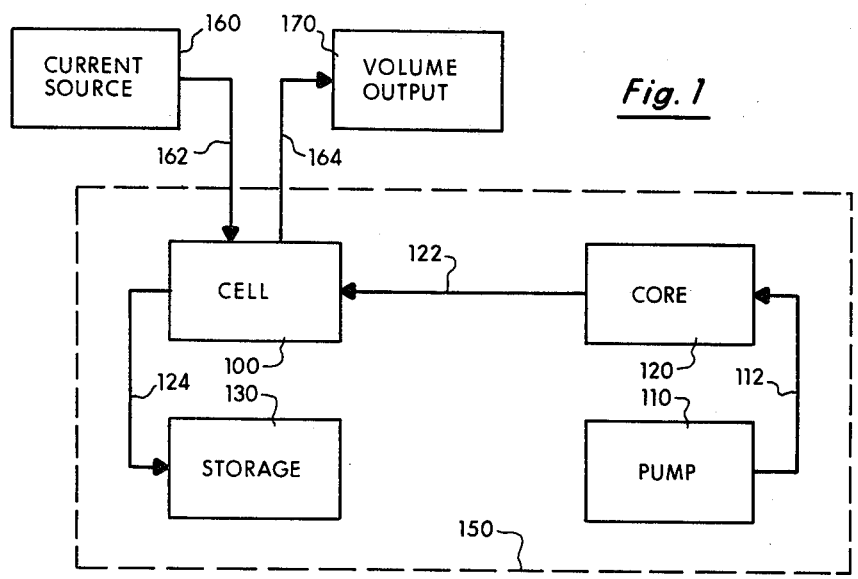
FIG. 1 is a block diagram illustrating the conductivity device of the present invention in an operational environment.

The cell 100 of the present invention is shown in FIG. 1 interconnected with a pump 110 and a container holding a permeable core plug 120 in a fluid circuit. In the preferred embodiment, a high pressure and high temperature oil and water mixture is passed through container 120 holding a core of sub-strata material in order to measure the relative permeability of the core. The fluid mixture passing through the core in container 120 is delivered through a fluid connection 122 into the cell 100 of the present invention which has as its purpose to determine the volume of oil and water contained in the fluid mixture. This mixture, after analysis, is delivered into a storage medium 130.

The purpose of cell 100 is to measure the practical flow of oil or water, one of the parameters required to calculate relative permeability of the core material held in container 120. The cell 100, the pump 110, the core container 120, and the storage container 130 are placed within a controlled environment commonly designated 150 in order to maintain a high pressure and high temperature environment. In the preferred embodiment, the temperature of the fluid mixture flowing into the cell 100 is typically in the range from 60° F. (15.5° C.) to 280° F. (138° C.) and the pressure is typically in the range from 100 psi ($6.89 \times 10^6$ dynes/cm$^2$) to 10,000 psi ($6.89 \times 10^8$ dynes/cm$^2$).

A current source 160 provides power to the cell 100 over leads 162 and the output of the cell 100 is delivered over leads 164 to a volume output circuit 170. The volume output circuit 170 accurately determines the volume of oil and water contained in the mixture found in fluid circuit 122.

Figure 2:
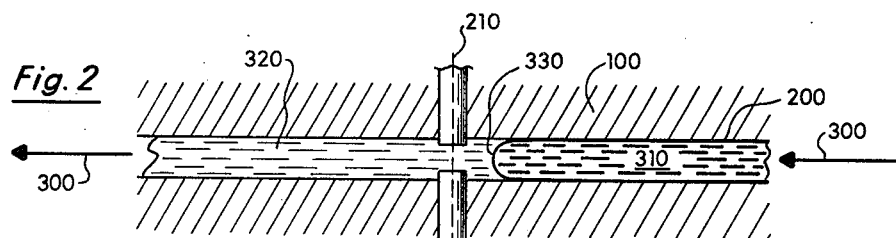
FIG. 2 is an illustration, in cross-section, of an oil droplet approaching the electrical probes of the present invention.
Figure 3:
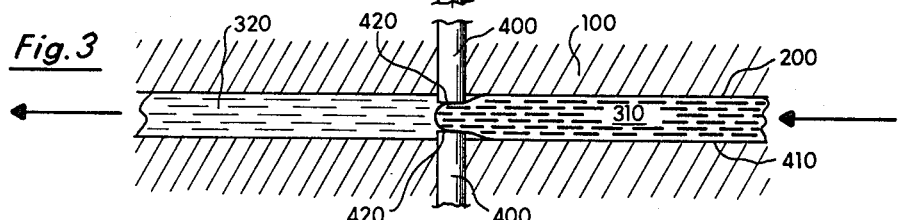
FIG. 3 is an illustration, in cross-section, of the oil droplet of FIG. 2 becoming distorted as it flows through the probes of the present invention.
Figure 4:
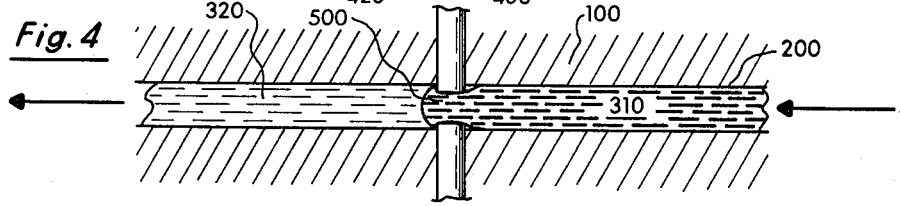
FIG. 4 is an illustration, in cross-section, of the oil droplet of FIG. 3 completely covering the probes of the present invention.

The principle of operation of the cell 100 of the present invention is best shown by reference to FIGS. 2 through 5 which shows a small passageway 200 with electrical probes 400 connected thereacross. When an oil and water mixture 300, or any fluid mixture containing immiscible fluids of different conductivity is forced to flow through a small bore hole or cylindrical passageway 200 as shown in FIG. 2, the mixed oil and water fluids separate into discrete oil droplets 310 and discrete water droplets 320. These droplets 310 and 320 are separated by a sharp oil/water interface 330. Oil and water have significantly different electrical conductivities, oil exhibits a low conductivity and water or brine exhibits a high conductivity.

Figure 5:
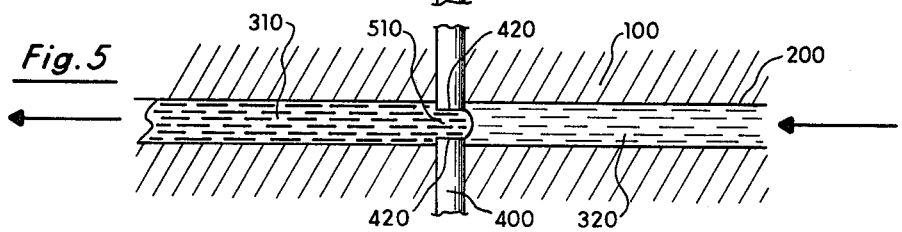
FIG. 5 is an illustration, in cross-section, of the oil droplet of FIG. 4 as it passes the probes of the present invention.

In FIGS. 2 through 5, the droplets 310 and 320 are flowing at an absolutely constant volumetric flow rate throughout the cell 100. As shown in FIG. 2, the interface 330 is substantially hemispherical. When, however, the interface 330 impacts upon two opposing electrical probes 400 connected across the interior of the passageway 200, the hemispherical interface 330 becomes distorted. Several effects are believed to occur during this time frame. First, by extending the two probe ends 400 into the interior passageway 410 of the passageway 200, the ends 420 are scoured free of any film buildup thus providing greater electrical connection with the flowing droplets. Secondly, not until the ends 420 of each probe are fully covered by an oil droplet 310 do the probes 400, when subjected to an electrical current, measure the conductivity of the oil. As shown in FIG. 5, when any portion of the probe end 420 is exposed to a water droplet 320 a path of high electrical conductivity is produced through the water 320.

In operation, therefore, by sensing the leading edge 500 of the oil droplet 310 and by sensing the lagging edge 510 of oil droplet 310, the time it takes between the detection of the leading edge 500 and the detection of the lagging edge 510 is proportional to the cumulative volume of the oil droplet that flowed past the plane 210 which is normal to the passageway 200. In the preferred embodiment, the diameter of the bore tube 200 is about 0.031 inch (approximately eight-tenths of a millimeter) and the diameter of the electrode 400 is approximately 0.020 inch (0.5 mm).

In the preferred embodiment, the electrodes are made from platinum and are oriented in plane 210. Platinum is utilized because of its high conductivity and its resistance to corrosion over long periods of time. Furthermore, the electrodes 210 are arranged to protrude into the flow path slightly as shown in FIGS. 2 through 5 in order to be scoured by the flow mixture 300. If the electrodes 400 were oriented to be flush with the sidewalls of the bore tube or passageway 200, little scouring effect would take place since the flow velocity along the sidewalls is low.

In summary, therefore, the passageway 200 of the present invention is of sufficient diameter to insure that the fluid mixture 300 flowing into the bore tube 200 will separate into discrete droplets. Diametrically opposed electrodes 400 are then oriented to slightly protrude into the flow path in order to measure the difference in conductivity between the water droplets 320 and the oil droplets 310. The interfaces 330 between the oil and water droplets can then be detected by accurately sensing the leading edge 500 of an oil droplet and the lagging edge 510 of that oil droplet. By measuring the difference in time between the leading and lagging edges (500 and 510) and by knowing the absolute volumetric flow rate of the fluid mixture 300, the volume of each oil droplet 310 and each water droplet 320 can be determined.

The cell 100 of the preferred embodiment is shown in FIG. 6. A machined body constructed from steel alloy or Hastelloy C material has formed therein the bore hole or passageway 200 and bores 602 and 604 on either end of passageway 200 of slightly larger diameter. The larger diameter bores 602 and 604 are interconnected with the smaller diameter bore 200 by means of tapers 606. The larger diameter bores 602 and 604 can be conventionally interconnected with fluid piping in order to deliver the fluid mixtures into the cell 100 so that it can be received by the bore holes 200. These connections 608 and 610 are tightly threaded to provide a high pressure fluid seal. Oriented in a plane perpendicular to the bore tube 200 are two electrodes 400 which are contained in the center of a compression nut 612 which threadedly engages the body 600. Each compression nut 612 compresses against a polysulfone ferrule 614.

The details of the body 600 are shown in FIGS. 7 and 8 to include the formed bore hole or passageway 200 and the bore holes 604 and 602 of larger diameter being connected therewith. Intersecting bore hole 200 with its formed passageway are a threaded female socket 700, a cylindrical chamber 710 for receiving the ferrule 614, a conical chamber 720 for also receiving the ferrule 614 and a smaller cylindrical chamber 730 also for receiving the ferrule 614. The threaded female socket 700 receives the compression nut 612.

In FIG. 9 is shown the compression nut 612 to include a threaded male portion 900 which engages the female socket 700 and a protruding cylindrical stem 910 which has for a diameter a value slightly less than the diameter of the cylindrical chamber 710.

In FIG. 10, are shown in the details of the ferrule 614 to include a cylinder 1000 having a diameter slightly less than the diameter of the stem 910 of the compression nut 612. The ferrule 614 can be made from any good flurocarbon or polysulfone exhibiting good chemical resistance against disintegration in a high pressure/high temperature oil and water environment and good resistance to mechanical deformation. At one end of the cylinder 1000 is a cap 1010 which, as shown in FIG. 6, abuts against the end 914 of the stem 910 of the compression nut 612. On the other end of the cylinder 1000 is a tapered region 1020 which corresponds in shape and configuration to the conical chamber 720 formed in the cell body 600 as shown in FIG. 8. And finally, the tapered region 1020 terminates in another cylinder 1030 having a diameter slightly less than the cylindrical chamber 730 formed in the cell body 600 as best shown in FIG. 8. Centrally disposed through the ferrule 614 is a formed passageway 1040 through which the electrode 400 is disposed.

In operation, the compression nut 612 firmly abuts against and compresses ferrule 614 into the formed chambers 710, 720, and 730 of the cell body 600 to provide a high pressure and high temperature fluid seal and to firmly hold the electrodes 400 in precise orientation. A sleeve of electrical insulation 630 surrounds the electrode 400 to insulate it from the compression nut 612.

In FIG. 12, the electronics of the present invention is set forth in block diagram form. A current source 1200 provides alternating current over lead 1202 to a step-up transformer 1210. In the preferred embodiment, the current source 1200 provides 10 KHz signal at approximately five volts peak-to-peak. The step-up transformer 1210 provides at its output on leads 1212, an approximately 150 volts peak-to-peak at a frequency at 10 KHz. However, operable frequencies could be utilized in a range of 5 to 20 KHz and operable voltages could be utilized in a range of 50 to 200 volts. If the frequency or voltage is too low deposits or film tends to build up on the probe ends due to polarization. By selecting the preferred frequency, the preferred voltage, and by slightly extending the probe ends into the passageway any film buildup is minimized. The buildup of film is undesirable in that inaccurate interface detection may result.

This signal is delivered across the cell 100 of the present invention by means of electrodes 400. This circuit is completed by means of a current limiting resistor 1220 which in the preferred embodiment is about one megohm.

When a high conductivity fluid such as water or brine is flowing through the cell 100, there is little voltage drop across the cell 100 and, therefore, substantially all the voltage is dropped across the limiting resistor 1220. On the other hand, when a low conductivity fluid such as oil is flowing through the cell 100, substantially all of the voltage from the transformer 1210 is delivered across the cell 100. Hence, the comparator 1230 senses the voltage dropped across the current limiting resistor 1220 and compares it to a reference level or threshold voltage. If the voltage signal appearing across the resistor 1220 exceeds the threshold level in comparator 1230, the comparator generates a first signal over lead 1232. Otherwise, if the voltage appearing across the current limiting resistor 1220 is below the predetermined threshold value, the comparator generates a second condition on lead 1232. These two signals on lead 1232 are delivered into a counter 1240 which counts the number of times the first signal appears on lead 1232 and delivers that count over lead 1242 into a readout circuit 1250. Likewise, the one-shot circuit 1260 which is also interconnected to lead 1232 counts the series of first pulses and delivers this count into a counter 1270 over lead 1262 which in turn is delivered into the readout 1250.

The operation of the circuitry shown in FIG. 12 will be discussed through reference to FIG. 13 wherein during a time sequence, the passage of several oil droplets flow past the plane 210 (electrodes 400) in the cell 100. These are shown graphically by FIG. 13a. It is important to note that the oil and water droplets 310 and 320 vary in length and in frequency. The electrical voltage output across the limiting resistor 1220 is shown in FIG. 13b as a series of pulses having lower amplitudes 1300 and higher amplitudes 1310. The higher amplitude pulses 1310 represent the larger voltage drop across current limiting resistor 1220 and hence the presence of water in the bore hole or passageway 200. The smaller amplitude sinusoidal signals represent the passage of a low conductivity material such as oil droplets 310 resulting in a higher voltage drop across the cell 100. The curve shown in FIG. 13c illustrates the output of comparator 1230 on lead 1232 which produces a series of pulses only when the pulses in FIG. 13b exceed the predetermined threshold level designated 1320. Whenever this occurs, a pulse is delivered on lead 1232. These pulses are counted by counter 1240 and as shown in FIG. 13d the number of pulses counted is proportional to the length of time or the time difference between successive oil droplets 310. Hence, the time between the leading edge 500 and the lagging edge 510 of oil droplets 310 can be accurately measured in the readout circuit 1250. It is to be recalled that this time difference is proportional to the volume of the oil droplet 310 since the absolute volumetric flow rate is constant. For example, if the absolute volumetric flow rate of the mixture is termed $V_m$ and the determined time difference is termed $\Delta t$, then the volume of a droplet, $V$, would be:

$$V = V_m(\Delta t)$$

Typical flow rates, in the preferred embodiment, are about 1 cc/min.

It is to be expressly understood that the voltage across the cell 100 could have been utilized to provide the necessary electrical information and that the pulses 1300 and 1310 could be conventionally inverted while still practicing the teachings of the present invention.

Furthermore, and as shown in FIG. 13b the pulses on lead 1232 can be utilized to drive a one-shot in circuit 1260 in order to provide a level corresponding to the start and finish of a water or oil droplet 310 and 320. In this situation, a counter 1270 counts the number of droplets in the mixture. This information is generally useful in evaluating experimental data and provides the number of oil droplets versus time.

Utilization of the preferred embodiment as set forth in the drawings has provided an accurate measurement of the volume of oil and water having errors in the order of one percent or less and with careful calibration of the detection level voltage errors of 0.2 percent or less.

Furthermore, because the interface between the water and oil droplets can either be convex or concave depending on the properties of the fluid and tubing, the detection level voltage can be adjusted upwardly or downwardly to give the most accurate measurement of the accumulative oil in a calibration test. However, because there is a large contrast between the output voltage of the water and oil, this accuracy is not terribly sensitive to the value of detection level voltage.

It is to be expressly understood that the cell conductivity device of the present invention can be suitably adapted to detect fluid mixtures other than that of oil and water wherein the differences in the fluid provide a sufficient difference in conductivity and provide, further, the sufficient interfacial edges as found between oil and water. It is to be further understood that although oil and water have been used as examples, any type of oil, such as crude, and any type of water, such as salt brine, is to be contemplated within the teachings of the present invention.

And, while the device of the present invention has been specifically set forth in the above disclosure, it is to be expressly understood that modifications and variations to both the method and the system can be made which would still fall within the scope and coverage of the appended claims herewith.

We claim:

1. A device for measuring the volume of each fluid in a fluid mixture, said fluid mixture flowing at a constant volumetric flow rate and each fluid in said mixture having a different electrical conductivity, said device comprising:
   means (600) receiving said mixture (300) for separating said mixture (300) in a formed passageway (200) into separate individual fluid droplets (310, 320), said separating means (600) being capable of maintaining said constant volumetric flow of said mixture (300), and
   means (400, 170) operatively interconnected with said separating means (600) for determining the time required for each droplet (310, 320) to flow through said passageway (200) by sensing the electrical conductivity of each droplet (310, 320) commencing with the leading interface (500) and ending with the lagging interface (510) as it passes through said passageway (200), said determined time being proportional to the volume of said droplet (310, 320).

2. The device of claim 1 wherein said determining means (160, 400, 170) comprises:
   means (400) mounted across said passageway (200) for generating electrical signals proportional to the electrical conductivity of each fluid droplet (310, 320) in a plane (210) perpendicular to the flow of said droplet (310, 320), and
   means (170) receptive of said electrical signals for measuring the time differences between said leading (500) and lagging (510) interfaces of each droplet (310, 320) as said droplet flows past said generating means (400).

3. The device of claim 2 wherein said generating means (400, 160) comprises:
   a current source (160),
   two opposing electrical probes (400) connected across the interior of said passageway for applying current from said current source (160) in said plane, and
   means (1220) interconnected with said current source (160) and said probes (400) for producing a voltage signal proportional to the conductivity of said droplets (310, 320).

4. The device of claim 3 wherein each of said probes (400) has an end (420) extending slightly into said passageway (200) so that the aforesaid end is scoured by said flowing mixture (300).

5. The device of claim 2 wherein said measuring means (170) comprises:
   means (1230) receptive of said electrical signals and of a predetermined threshold level for producing a first signal (1310) representative of low conductivity fluid when said electrical signals exceed said threshold level (1320) and for producing a second signal (1300) representative of high conductivity fluid when said electrical signals are below said threshold level (1320), and
   means (1240, 1250) receptive of said first and second signals for determining said time difference between the transition from said second signal to said first signal and the transition from said first signal to said second signal.

6. A device for measuring the volume of each fluid in a fluid mixture (300), said fluid mixture (300) flowing at a constant volumetric flow rate and each fluid having a different electrical conductivity, said device comprising:
   means (600) receiving said mixture (300) for separating said mixture (300) in a formed cylindrical passageway (200) into separate individual fluid droplets (310, 320), said separating means (600) being capable of maintaining said constant flow of said mixture (300),
   an alternating current source (160),
   two opposing electrical probes (400) connected across the interior of said passageway (200) for applying current from said current source (160) to said droplets (310, 320) in a plane (210) perpendicular to the flow of said droplets (310, 320),
   means (1220) interconnected with said current source (1200) and said probes (400) for producing a voltage signal proportional to the conductivity of said droplets (310, 320), means (1230) receptive of said voltage signals and of a predetermined threshold level for producing a first signal (1310) representative of a low conductivity fluid when said voltage signals exceed said threshold level (1320) and for producing a second signal (1300) representative of a high conductivity fluid when said electrical signals are below said threshold level (1320), and means (1240, 1250) receptive of said first and second signals for determining the volume of each of said droplet by measuring the time difference between the leading and lagging interfaces of each droplet as said droplet flows past said generating means, said measured time difference being proportional to the volume of said droplet.

7. The device of claim 6 wherein each of said probes (400) has an end (420) extending slightly into said passageway (200) so that the aforesaid end is scoured by said flowing mixture (300).

8. A device for measuring the volumes of oil (310) and water (320) in an oil and water mixture (300), said oil and water mixture flowing at a constant volumetric flow rate, said device comprising:

means (600) receiving said mixture for separating said mixture (300) in a formed passageway (200) into separate oil and water droplets (310, 320), said separating means (600) being capable of maintaining said constant flow of said mixture (300), an alternating current source (1200), two opposing electrical probes (400) connected across the interior of said passageway (200) for applying current from said current source to said oil and water droplets (310, 320) in a plane (210) substantially perpendicular to the flow of said droplets (310, 320), means (1220) interconnected with said current source (1200) and said probes (400) for producing a voltage signal proportional to the conductivity of said oil and water droplets (310, 320), means (1230) receptive of said voltage signals and of a predetermined threshold level for producing a first signal (1310) representative of water (300) when said voltage signals exceed said threshold level (1320) and for producing a second signal (1300) representative of oil (310) when said electrical signals are below said threshold level (1320), and means receptive of said first and second signals (1300, 1310) for determining the volume of each of said oil and water droplets (310, 320) by measuring the time difference between the leading (500) and lagging (510) interfaces of each droplet as said droplet flows past said probes, said measured time difference being proportional to the volume of said droplet.

9. The device of claim 8 wherein said alternating current source (1200) has a frequency in the range of approximately 5 to 20 KHz and a voltage in the range of approximately 50-150 volts.

10. A device for measuring the volumes of oil (310) and water (320) in an oil and water mixture (300), said oil and water mixture (300) flowing at a constant volumetric flow rate, said device comprising:

means (600) receiving said mixture (300) for separating said mixture (300) in a formed passageway (200) into separate oil (310) and water (320) droplets, said separating means (600) being capable of maintaining said constant flow of said mixture, an alternating current source (1200), means (400) interconnected with said current source (1200) and connected across the interior of said passageway (200) for producing a voltage signal proportional to the conductivity of said oil and water droplets as said droplets flow past said interior connection, means receptive of said voltage signals for determining the volume of each of said oil and water droplets by measuring the time difference between the leading (500) and lagging (510) interfaces of each droplet as said droplet flows past said interior connection, said measured time difference being proportional to the volume of said droplet.

11. A method for measuring the volumes of oil and water in an oil and water mixture, said oil and water mixture (300) flowing at a constant volumetric flow rate, said method comprising the steps of:

separating said mixture (300) into separate oil (310) and water (320) droplets while maintaining said constant volumetric flow rate, sensing the leading (500) and lagging (510) interfaces of each separated droplet by detecting the electrical conductivity of the aforesaid droplet, and measuring the time difference between said leading (500) and lagging (510) edges so that the volume of said droplet can be determined.

12. A device for measuring the volume of each fluid in a fluid mixture, said fluid mixture flowing at a constant volumetric flow rate and each fluid in said mixture having a different electrical conductivity, said device comprising:

means (600) receiving said mixture (300) for separating said mixture (300) in a formed passageway (200) into separate individual fluid droplets (310, 320), said separating means (600) being capable of maintaining said constant volumetric flow of said mixture (300), and means (400, 170) operatively interconnected with said separating means (600) for determining the time required for each droplet (310, 320) to flow through said passageway (200) by sensing the electrical conductivity of each droplet (310, 320) as it passes through said passageway (200), said determined time being proportional to the volume of said droplet (310, 320), said determining means comprising:

(a) means (400) mounted across said passageway (200) for generating electrical signals proportional to the electrical conductivity of each fluid droplet (310, 320) in a plane (210) perpendicular to the flow of said droplet (310, 320), said generating means having an alternating current source (1200) with a frequency in the range of approximately 5 to 20 KHz and a voltage in the range of approximately 50-150 volts; two opposing electrical probes (400) connected across the interior of said passageway for applying current from said alternating current source (1200) in said plane, and means (1220) interconnected with said alternating current source (1200) and said probes (400) for producing a voltage signal proportional to the conductivity of said droplets (310, 320), and (b) means (170) receptive of said electrical signals for measuring the time differences between the leading (500) and lagging (510) interfaces of each droplet (310, 320) as said droplet flows past said generating means (400).

* * * * *